United States Patent
Kolter et al.

(10) Patent No.: US 9,555,002 B2
(45) Date of Patent: Jan. 31, 2017

(54) SOLID PHARMACEUTICAL PREPARATIONS CONTAINING COPOLYMERS BASED ON POLYETHERS COMBINED WITH POORLY WATER-SOLUBLE POLYMERS

(75) Inventors: Karl Kolter, Limburgerhof (DE); Dejan Djuric, Mannheim (DE); Stefan Fischer, Freinscheim (DE)

(73) Assignee: BASF SE, Ludwigshafen (DE)

( * ) Notice: Subject to any disclaimer, the term of this patent is extended or adjusted under 35 U.S.C. 154(b) by 777 days.

(21) Appl. No.: 13/319,575

(22) PCT Filed: May 11, 2010

(86) PCT No.: PCT/EP2010/056447
§ 371 (c)(1),
(2), (4) Date: Nov. 9, 2011

(87) PCT Pub. No.: WO2010/130728
PCT Pub. Date: Nov. 18, 2010

(65) Prior Publication Data
US 2012/0053248 A1 Mar. 1, 2012

(30) Foreign Application Priority Data
May 13, 2009 (EP) .................................... 09160129

(51) Int. Cl.
| A61K 9/00 | (2006.01) |
| A61K 47/32 | (2006.01) |
| A61K 47/34 | (2006.01) |
| A61K 47/30 | (2006.01) |
| A61K 47/22 | (2006.01) |
| A61K 9/20 | (2006.01) |
| C08F 283/06 | (2006.01) |

(52) U.S. Cl.
CPC ........... *A61K 9/2095* (2013.01); *A61K 9/2027* (2013.01); *A61K 9/2031* (2013.01); *A61K 9/2054* (2013.01); *C08F 283/06* (2013.01)

(58) Field of Classification Search
CPC .. A61K 9/2095; A61K 9/2027; A61K 9/2031; A61K 9/2054; C08F 283/06
USPC ................. 514/772.6, 772.4, 772.7; 424/400
See application file for complete search history.

(56) References Cited

U.S. PATENT DOCUMENTS

| 6,075,107 A | 6/2000 | Kothrade et al. |
| 6,271,307 B1 | 8/2001 | Huff et al. |
| 6,331,294 B1 | 12/2001 | Meffert et al. |
| 6,867,262 B1 | 3/2005 | Angel et al. |
| 2007/0148232 A1 | 6/2007 | Crew et al. |
| 2008/0248117 A1* | 10/2008 | Kolter et al. ................. 424/486 |
| 2008/0293828 A1 | 11/2008 | Bouillo et al. |
| 2010/0204425 A1 | 8/2010 | Mertoglu et al. |
| 2010/0280047 A1 | 11/2010 | Kolter et al. |
| 2011/0178183 A1 | 7/2011 | Meyer-Boehm et al. |
| 2011/0195118 A1 | 8/2011 | Kolter et al. |
| 2011/0256193 A1 | 10/2011 | Meyer-Bohm et al. |

FOREIGN PATENT DOCUMENTS

| DE | 19935063 | 2/2001 |
| EP | 0876819 | 11/1998 |
| EP | 0948957 | 10/1999 |
| EP | 0953347 | 11/1999 |
| WO | WO-2007/051743 | 5/2007 |
| WO | WO-2009/013202 | 1/2009 |
| WO | WO-2010/112489 | 10/2010 |
| WO | WO-2010/130728 | 11/2010 |

OTHER PUBLICATIONS

Suzuki et al. (Solid Dispersions of Benidipine Hydrochloride. I. Preparations Using Different Solvent Systems and Dissolution Properties, Chem. Pharm. Bull. 44 (2): 364-371 (1996)), 8 pages.*
Hasegawa et al. (Physical Properties of Solid Dispersions of Poorly Water-Soluble Drugs with Enteric Coating Agents, Chem. Pharm. Bull., 33(8): 3429-3435 (1985)), 7 pages.*
International Preliminary Report on Patentability (World Intellectual Property Organization, Nov. 29, 2011) (English Translation), 8 pages.*
Yuan, J. et al., "Influence of solid dispersion technique combination on dissolution of tanshinone IIA", vol. 34 2009 , 685-689.
"PCT International Search Report for PCT/EP2010/056447", Feb. 10, 2011 , 3 pages.
Leuner, Christian et al., "Improving Drug Solubility for Oral Delivery Using Solid Dispersions", *European Journal of Pharmaceutics and Biopharmaceutics*, vol. 50 2000 , 47-60.

* cited by examiner

*Primary Examiner* — Anna Pagonakis
*Assistant Examiner* — Miriam A Levin
(74) *Attorney, Agent, or Firm* — Servilla Whitney LLC

(57) ABSTRACT

The invention relates to dosage forms which contain preparations of poorly water-soluble substances in a polymer matrix of polyether copolymers, said polyether copolymers being obtained by the radically initiated polymerization of a mixture from 30 to 80% by weight of N-vinyl lactam, 10 to 50% by weight of vinyl acetate and 10 to 50% by weight of a polyether, and at least one poorly water-soluble polymer, the poorly water-soluble substance being present in the polymer matrix as an amorphous substance.

11 Claims, No Drawings

SOLID PHARMACEUTICAL PREPARATIONS CONTAINING COPOLYMERS BASED ON POLYETHERS COMBINED WITH POORLY WATER-SOLUBLE POLYMERS

CROSS-REFERENCE TO RELATED APPLICATIONS

This application is the National Stage entry of PCT/EP2010/056447, filed on May 11, 2010, which claims priority to European Patent application number 09160129.4, filed on May 13, 2009, both of which are incorporated herein by reference in their entireties.

BACKGROUND

Field of the Invention

The present invention relates to solid pharmaceutical preparations of polyether copolymers, which are obtained by polymerization of vinyl acetate and N-vinyllactams in the presence of a polyether, and slightly water-soluble active substances, in combination with further polymers which are capable of influencing the stability of the formulation and/or the release of the biologically active substance. Furthermore, the invention relates to processes for the production of these preparations and the use thereof.

The corresponding polyether copolymers act as solubilizers for the slightly water-soluble biologically active substances.

Background Information

In the production of homogeneous preparations, in particular of biologically active substances, the solubilization of hydrophobic, i.e. slightly water-soluble, substances has become very important in practice.

Solubilization is to be understood as meaning the imparting of solubility to substances which are slightly soluble or insoluble in a certain solvent, in particular water, by surface-active compounds, the solubilizers. Such solubilizers are capable of converting poorly water-soluble or water-insoluble substances into transparent, at most opalescent aqueous solutions without the chemical structure of these substances undergoing a change thereby (cf. Römpp Chemie Lexikon, 9th edition, vol. 5. page 4203, Thieme Verlag, Stuttgart, 1992).

In the solubilizates prepared, the poorly water-soluble or water-insoluble substance is present as a colloidal solution in the molecular associates of the surface-active compounds which form in aqueous solution, such as, for example, hydrophobic domains or micelles. The resulting solutions are stable or metastable single-phase systems which appear optically transparent to opalescent.

In the case of pharmaceutical preparations, the bioavailability and hence the action of drugs can be increased by the use of solubilizers.

A further desirable requirement regarding solubilizers is the ability to form so-called "solid solutions" with slightly soluble substances. The term "solid solution" designates a state in which a substance is dispersed in colloidal form or ideally dispersed in molecular form in a solid matrix, for example a polymer matrix. Such solid solutions, for example when used in solid pharmaceutical administration forms of a slightly soluble active substance, lead to improved release of the active substance. An important requirement regarding said solid solutions is that they are stable even on storage over a relatively long time, i.e. that the active substance does not crystallize. Furthermore, the capacity of the solid solution, in other words the ability to form stable solid solutions having active substance contents which are as high as possible, is also important.

In the formation of solid solutions, the hygroscopicity of the solubilizers also plays an important role in addition to the basic ability of the solubilizers to form solid solutions. Solubilizers which take up too much water from the surrounding air lead to deliquescence of the solid solution and the undesired crystallization of the active substances. Excessively high hygroscopicity can also lead to problems during the processing to give administration forms.

Many known polymeric solubilizers have the disadvantages that they do not form stable solid solutions, in particular when the active substance is present above the saturated concentration in the polymer. As a result, the system is kinetically controlled and the active substance is crystallized in the course of storage. This presents a major problem.

In addition, the known solubilizers and formulations still leave room for improvements, which relates to the solubilization in aqueous systems, in particular biological systems. The oral bioavailability is frequently not increased to the extent which would be desirable in order to achieve a uniform, reproducible action without side effects. Regarding the processability, too, some of the known solubilizers have disadvantages owing to their tendency to become tacky, since they are not sufficiently flowable powders.

A further problem in the case of pharmaceutical preparations of slightly water-soluble active substances is the control of the release. Frequently, it is not the excipient that controls the release in the case of such forms but the crystal properties of the active substance. This means that variations in the particle size of the active substance, differences in the crystal modification and differences in the particle shape have a considerable influence on the dissolution. Since these parameters are difficult to establish exactly, different release rates result. In the case of water-soluble active substances, this problem is not present since the dissolution process of the active substance is considerably faster than the diffusion process which is controlled by a retardant polymer.

With regard to the release, a distinction should be made between instant release (fast-releasing) forms, enteric release (gastric resistant) forms and sustained release (delayed, slowly releasing) forms. Forms which release at least 75% after 1 h are designated as instant release forms. In the case of enteric release forms, slight release takes place in gastric juice (<10% as a rule) but fast release in intestinal fluid.

Sustained release forms have a slow release both in gastric juice and in intestinal fluid. The term sustained release form is used when the release is slower than 75% after 3 h.

The slightly water-soluble polymers are to be understood as meaning polymers which are slightly soluble over the entire pH range or at least in a certain pH range. These include so-called sustained release polymers (insoluble as a rule from pH 1 to 14), acidic, gastric resistant polymers (slightly soluble in the acidic pH range), and basic, reverse enteric polymers (slightly soluble in the neutral to basic pH range). See further below for a definition of solubility.

EP-A 876 819 describes the use of copolymers of at least 60% by weight of N-vinylpyrrolidone and amides or esters having long-chain alkyl groups.

EP-A 948 957 describes the use of copolymers of monoethylenically unsaturated carboxylic acids, such as, for example, acrylic acid, and hydrophobically modified comonomers, such as, for example, N-alkyl- or N,N-dialkylamides of unsaturated carboxylic acids having $C_8$-$C_{30}$-alkyl radicals.

DE-A 199 350 63 discloses polyalkylene oxide-containing graft polymers based on vinyllactams and vinyl acetate and the use thereof as gas hydrate inhibitors.

EP-A 953 347 discloses the use of polyalkylene oxide-containing graft polymers as solubilizers. The graft polymers which are described there and comprise vinyl acetate and polyalkylene oxides are frequently not powders but viscous tacky liquids, which is a disadvantage in use.

WO 2007/051743 discloses the use of water-soluble or water-dispersible copolymers of N-vinyllactam, vinyl acetate and polyethers as solubilizers for pharmaceutical, cosmetic, food, agrotechnical and other technical applications. It is stated therein very generally that the corresponding graft polymers can also be processed in the melt with the active substances.

WO 2009/013202 discloses that such graft polymers of N-vinyllactam, vinyl acetate and polyethers can be melted in an extruder and mixed with pulverulent or liquid active substances, the extrusion at temperatures substantially below the melting point of the active substance being described.

However, a satisfactorily high and simultaneously stable active substance loading cannot be achieved by mixing the molten graft polymers with pulverulent or liquid active substances. In particular, the achievement of a stable X-ray amorphous state of the active substance is not always possible to satisfactory degrees.

SUMMARY

Embodiments of the present invention are directed toward a dosage form comprising preparations of slightly water-soluble active substances in a polymer matrix of polyether copolymers, the polyether copolymers being obtained by free radical polymerization of a mixture of from 30 to 80% by weight of N-vinyllactam, from 10 to 50% by weight of vinyl acetate and from 10 to 50% by weight of a polyether, and of at least one water-soluble polymer in which the slightly water-soluble active substance is present in amorphous form in the polymer matrix.

In one or more embodiments, the slightly water-soluble polymers are those polymers whose solubility in water is pH-dependent. The slightly water-soluble polymers can be based on acrylic or methacrylic acid or esters thereof, or mixtures of said monomers.

In specific embodiments, the slightly water-soluble polymers comprise homo- and copolymers of vinyl acetate, and ethylcelluloses.

Other embodiments are directed to a process for the production of preparations for dosage forms of slightly water-soluble active substances, the active substances being present in amorphous for embedded in a polymer matrix based on polyether copolymers of from 30 to 80% by weight of N-vinyllactam, from 10 to 50% by weight of vinyl acetate and from 10 to 50% by weight of a polyether, wherein, in addition to the polyether copolymer, at least one slightly water-soluble polymer is incorporated into the polymer matrix, and the polymers are thoroughly mixed with the slightly water-soluble active substances.

DETAILED DESCRIPTION

It was an object of the present invention to provide improved preparations of slightly water-soluble active substances, which preparations permit targeted adjustment of the release in combination with good bioavailability.

Accordingly, pharmaceutical dosage forms comprising preparations of slightly water-soluble active substances in a polymer matrix of polyether copolymers, the polyether copolymers being obtained by free radical polymerization of a mixture of from 30 to 80% by weight of N-vinyllactam, from 10 to 50% by weight of vinyl acetate and from 10 to 50% by weight of a polyether, and of at least one slightly water-soluble polymer in which the slightly water-soluble active substance is present in amorphous form in the polymer matrix were found.

Furthermore, a process for the production of preparations of slightly water-soluble active substances was found, the active substances being present in amorphous form embedded in a polymer matrix based on polyether copolymers of from 30 to 80% by weight of N-vinyllactam, from 10 to 50% by weight of vinyl acetate and from 10 to 50% by weight of a polyether, wherein, in addition to the polyether copolymer, at least one slightly water-soluble polymer is incorporated into the polymer matrix, and the polymers are thoroughly mixed with the slightly water-soluble active substances.

The polyether copolymers present in the polymer matrix are obtained by free radical polymerization of a mixture of
  i) from 30 to 80% by weight of N-vinyllactam,
  ii) from 10 to 50% by weight of vinyl acetate and
  iii) from 10 to 50% by weight of a polyether,
with the proviso that the sum of i), ii) and iii) is equal to 100% by weight.

According to one process variant, the polyether copolymers are thoroughly mixed with slightly water-soluble polymers and the slightly water-soluble active substances and the mixture is heated above the glass transition temperature of the copolymers.

According to a further process variant, the mixture of polymers and active substances is prepared in organic solution and then dried.

The polyether copolymers are freely soluble in water, which means that, at 20° C., 1 part of copolymer dissolves in from 1 to 10 parts of water.

According to one embodiment of the invention, preferred polyether copolymers, obtained from:
  i) 30 to 70% by weight of N-vinyllactam
  ii) 15 to 35% by weight of vinyl acetate, and
  iii) 10 to 35% by weight of a polyether,
are used.

Particularly preferably used polyether copolymers are obtainable from:
  i) 40 to 60% by weight of N-vinyllactam
  ii) 15 to 35% by weight of vinyl acetate, and
  iii) 10 to 30% by weight of a polyether.

Very particularly preferably used polyether copolymers are obtainable from
  i) 50 to 60% by weight of N-vinyllactam
  ii) 25 to 35% by weight of vinyl acetate, and
  iii) 10 to 20% by weight of a polyether.

The proviso that the sum of the components i), ii), and iii) is equal to 100% by weight also applies to the preferred and particularly preferred compositions.

Suitable N-vinyllactam is N-vinylcaprolactam or N-vinylpyrrolidone or a mixture thereof. N-Vinylcaprolactam is preferably used.

Polyethers serve as a grafting base. Preferred polyethers are polyalkylene glycols. The polyalkylene glycols may have molecular weights of from 1000 to 100 000 D [Dalton], preferably from 1500 to 35 000 D, particularly preferably from 1500 to 10 000 D. The molecular weights are determined starting from the OH number measured according to DIN 53240.

Particularly preferred polyalkylene glycols are polyethylene glycols. Furthermore, polypropylene glycols, polytetrahydrofurans or polybutylene glycols, which are obtained from 2-ethyloxirane or 2,3-dimethyloxirane, are also suitable.

Other suitable polyethers are random or block copolymers of polyalkylene glycols obtained from ethylene oxide, propylene oxide and butylene oxides, such as, for example, polyethylene glycol-polypropylene glycol block copolymers. The block copolymers may be of the AB type or of the ABA type.

The preferred polyalkylene glycols also include those which are alkylated at one terminal OH group or at both terminal OH groups. Suitable alkyl radicals are branched or straight-chain $C_1$- to $C_{22}$-alkyl radicals, preferably $C_1$-$C_{18}$-alkyl radicals, for example methyl, ethyl, n-butyl, isobutyl, pentyl, hexyl, octyl, nonyl, decyl, dodecyl, tridecyl or octadecyl radicals.

General processes for the preparation of the polyether copolymers according to the invention are known per se. The preparation is effected by free radical polymerization, preferably in solution, in nonaqueous, organic solvents or in mixed nonaqueous/aqueous solvents. Suitable preparation processes are described, for example, in WO 2007/051743 and WO 2009/013202, the disclosure of which regarding the preparation process is hereby incorporated by reference.

For the targeted control of the release, the copolymers having the solubilizing effect are used in combination with slightly water-soluble polymers which are suitable for influencing the release of the biologically active substance. The extent to which the release is influenced depends here as a rule on the concentration of the slightly water-soluble polymer.

The ratio of the polyether copolymer to the slightly water-soluble polymer may be from 99:1 to 10:90. Preferably, it is from 90:10 to 30:70 and particularly preferably from 80:20 to 40:60.

Regarding the solubility of the polymers, the term "slightly water-soluble" is to be understood as follows: according to the invention, the term "slightly water-soluble" comprises slightly soluble and also practically insoluble substances and means that, for a solution of the polymer in water at 20° C., from at least 100 to 1000 g of water are required per g of polymer. In the case of practically insoluble substances, at least 10 000 g of water are required per g of substance.

In the following description of the slightly water-soluble polymers, the term "slightly water-soluble" is abbreviated to "slightly soluble".

Slightly Water-Soluble Polymers

In the context of the invention, slightly water-soluble polymers are either neutral slightly soluble polymers (sustained release polymers), anionic slightly soluble polymers (gastric resistant polymers) or basic slightly soluble polymers.

Neutral Slightly Soluble Polymers

Slightly soluble polymers are understood as meaning those polymers which are slightly water-soluble or only swellable in water over the total pH range from 1 to 14. As a rule, the pharmaceutical composition comprises only one water-insoluble polymer. However, two or more water-insoluble polymers may also be present alongside one another or as a mixture.

Examples of suitable slightly soluble polymers are:

Neutral or substantially neutral methacrylate copolymers. These may comprise in particular at least 95, in particular at least 98, preferably at least 99, especially at least 99, particularly preferably 100, % by weight of (meth)acrylate monomers subjected to free radical polymerization and having neutral radicals, in particular C1- to C4-alkyl radicals.

Suitable (meth)acrylate monomers having neutral radicals are, for example, methyl methacrylate, ethyl methacrylate, butyl methacrylate, methyl acrylate, ethyl acrylate, butyl acrylate. Methyl methacrylate, ethyl acrylate and methyl acrylate are preferred. Methacrylate monomers having anionic radicals, e.g. acrylic acid and/or methacrylic acid, may be present in small proportions of less than 5, preferably not more than 2, particularly preferably not more than 1 or from 0.05 to 1% by weight.

For example, neutral or virtually neutral (meth)acrylate copolymers of from 20 to 40% by weight of ethyl acrylate, from 60 to 80% by weight of methyl methacrylate and from 0 to less than 5, preferably from 0 to 2 or from 0.05 to 1, % by weight (Eudragit® NE type) are suitable. Eudragit NE is a copolymer of 30% by weight of ethyl acrylate and 70% by weight of methyl methacrylate.

Further suitable slightly soluble (meth)acrylate copolymers are, for example, polymers which are soluble or swellable independently of pH and which are suitable for drug coatings.

The slightly soluble polymer may be a polymer of from 98 to 85% by weight of C1- to C4-alkyl esters of acrylic or of methacrylic acid and from 2 to 15% by weight of (meth)acrylate monomers having a quaternary ammonium group or a mixture of a plurality of polymers of this class of substance.

The slightly soluble polymer may also be a polymer of from 97 to more than 93% by weight of C1- to C4-alkyl esters of acrylic or of methacrylic acid and from 3 to less than 7% by weight of (meth)acrylate monomers having a quaternary ammonium group (Eudragit® RS type).

Preferred C1- to C4-alkyl esters of acrylic or of methacrylic acid are methyl acrylate, ethyl acrylate, butyl acrylate, butyl methacrylate and methyl methacrylate.

2-Trimethylammoniumethyl methacrylate chloride is particularly preferred as a (meth)acrylate monomer having quaternary amino groups.

A suitable copolymer by way of example comprises 65% by weight of methyl methacrylate, 30% by weight of ethyl acrylate and 5% by weight of 2-trimethylammoniumethyl methacrylate chloride (Eudragit RS).

The slightly soluble polymer may be a polymer of from 93 to 88% by weight of C1- to C4-alkyl esters of acrylic or of methacrylic acid and from 7 to 12% by weight of (meth)acrylate monomers having a quaternary ammonium group (Eudragit RL type). A specifically suitable copolymer comprises, for example, 60% by weight of methyl methacrylate, 30% by weight of ethyl acrylate and 10% by weight of 2-trimethylammoniumethyl methacrylate chloride (Eudragit® RL).

The water-insoluble polymer may be a mixture of polymers of the Eudragit RS type and of the Eudragit RL type in the ratio of from 20:1 to 1:20.

Mixtures of Eudragit RS and Eudragit RL, for example in the ratio of from 20:1 to 1:20 parts by weight, are also particularly suitable.

The pharmaceutical composition may also comprise a polyvinyl acetate as the slightly soluble polymer. Suitable polyvinyl acetates are, for example, the homopolymers of vinyl acetate. Furthermore, slightly soluble polyvinyl acetate copolymers are suitable, for example water-insoluble copolymers of vinyl acetate and N-vinylpyrrolidone.

Commercially available polyvinyl acetates are, for example, Kollicoat® SR 30D or Kollidon® SR.

Other suitable slightly soluble polymers are alkylcelluloses, such as, for example, ethylcellulose.

Anionic Slightly Soluble Polymers

Furthermore, anionic slightly soluble polymers may also be used. Anionic polymers are understood as meaning preferably polymers having at least 5%, particularly preferably from 5 to 75%, of monomer radicals with anionic groups. Anionic (meth)acrylate copolymers are preferred. Suitable commercially available (meth)acrylate copolymers having anionic groups are, for example, the Eudragit® types L, L100-55, S and FS. Suitable anionic (meth)acrylate copolymers are, for example, polymers of from 25 to 95% by weight of C1- to C4-alkyl esters of acrylic or of methacrylic acid and from 5 to 75% by weight of (meth)acrylate monomers having an anionic group. Depending on the content of anionic groups and the character of the further monomers at a pH above pH 5.0, appropriate polymers are water-soluble and hence also soluble in intestinal fluid. As a rule, said proportions sum to 100% by weight.

A (meth)acrylate monomer having an anionic group may be, for example, acrylic acid, but preferably methacrylic acid.

Furthermore, anionic (meth)acrylate copolymers of from 40 to 60% by weight of methacrylic acid and from 60 to 40% by weight of methyl methacrylate or from 60 to 40% by weight of ethyl acrylate are suitable (Eudragit L or Eudragit L100-55 types).

Eudragit L is a copolymer of 50% by weight of methyl methacrylate and 50% by weight of methacrylic acid.

Eudragit L100-55 is a copolymer of 50% by weight of ethyl acrylate and 50% by weight of methacrylic acid. Eudragit L 30D-55 is a dispersion comprising 30% by weight of Eudragit L100-55.

Also suitable are anionic (meth)acrylate copolymers of from 20 to 40% by weight of methacrylic acid and from 80 to 60% by weight of methyl methacrylate (Eudragit® S type).

For example, anionic (meth)acrylate copolymers consisting of from 10 to 30% by weight of methyl methacrylate, from 50 to 70% by weight of methyl acrylate and from 5 to 15% by weight of methacrylic acid (Eudragit® FS type) are furthermore suitable. Eudragit FS is a copolymer of 25% by weight of methyl methacrylate, 65% by weight of methyl acrylate and 10% by weight of methacrylic acid. Eudragit FS 30 D is a dispersion comprising 30% by weight of Eudragit® FS.

The copolymers preferably comprise substantially to exclusively the monomers methacrylic acid, methyl acrylate and ethyl acrylate in the abovementioned proportions. However, small amounts in the range from 0 to 10, e.g. from 1 to 5, % by weight of further vinylically copolymerizable monomers, such as, for example, methyl methacrylate, butyl methacrylate, butyl acrylate or hydroxyethyl methacrylate, may additionally be present without this leading to impairment of the essential properties.

The copolymers can be prepared by conventional continuous or batch free radical mass, solution, bead or emulsion polymerization processes in the presence of free radical initiators and, if appropriate, chain-transfer agents for adjusting the molecular weight. The average molecular weight Mw (weight average, determined, for example, by measuring the solution viscosity) may be, for example, in the range from 80 000 to 1 000 000 (g/mol). Emulsion polymerization in the aqueous phase in the presence of water-dissolved initiators and (preferably anionic) emulsifiers is preferred. In the case of mass polymerization, the copolymer may be processed in solid form by crushing, extrusion, granulating or hot face cutting.

Also suitable as anionic polymer is hydroxypropyl methylcellulose acetate succinate, a gastric resistant polymer which is soluble under basic conditions.

Basic Slightly Soluble Polymers

It is also possible to use basic polymers, such as basic meth(acrylates) or chitosan. An example of a corresponding commercially available polymer is Eudragit® E or EPO, which is a copolymer of methyl methacrylate, butyl methacrylate and dimethylaminoethyl methacrylate.

The solid preparations can be prepared by methods known per se.

According to one embodiment, all ingredients of the preparations are initially brought into solution together in a suitable solvent and the solvent is then removed. Solvents which may be used are all solvents customary in pharmaceutical technology, for example ethanol, isopropanol, n-butanol, isobutanol, ethyl acetate, acetone or dimethylformamide. The removal of the solvents can be effected via all possible types of drying processes, for example via spray drying, fluidized-bed drying, drum drying, drying with the use of supercritical gases, freeze-drying, evaporation.

According to a preferred procedure, the solid preparations are prepared by extrusion.

The polymers can be fed to the extruder both in pulverulent form and in the form of solutions or dispersions.

The dispersions or solutions of the polymers can be converted into the molten state by removal of the dispersing medium or solvent in an extruder and into a solid form by cooling of the melt.

The melt thus obtained can then be cooled and granulated. For this purpose, so-called hot face cutting or cooling under air or inert gas, for example on a Teflon belt or chain belt, and subsequent granulation of the cooled melt strand are effected. However, cooling can also be effected in a solvent in which the polymers are not significantly soluble.

The following methods A-E are in principle used:

A Physical powder mixture comprising polymers and active substance and feeding of this polymer mixture into the extruder
B Feeding of the active substance via a separate bypass into nonmolten polymer mixture
C Feeding of the active substance via a side metering means into molten polymers
D Polymer solution with active substance dissolved or dispersed therein, in partly devolatilized polymer melt or nonmolten polymer mixture;
E Processes according to A-D, solvent additionally being introduced into the extruder and evaporated again In principle, the customary extruder types known to a person skilled in the art are suitable for the process according to the invention. These usually comprise a housing, a drive unit with transmission and a process unit which consists of the extruder shaft or extruder shafts equipped with the screw elements, a modular design being assumed in this case.

The extruder consists of a plurality of sections, which in each case are to be coordinated with certain process units. Each of these sections consists of one or more barrels (barrel blocks) as a smallest independent unit and the associated screw sections with the screw elements corresponding to the object of the process.

The individual barrels should be heatable. Furthermore, the barrels can also be designed for cooling, for example for cooling with water. The individual barrel blocks are preferably heatable and coolable independently of one another, so that different temperature zones can be established also along the extrusion direction.

The extruder is advantageously in the form of a twin-screw extruder having corotating screws. The screw configuration may provide different degrees of shearing depending on the product. Kneading elements must be used in particular in the melting zone. It is also possible to use reverse kneading elements.

Suitable twin-screw extruders may have a screw diameter of from 16 to 70 mm and a length of from 25 to 40 D.

The total extruder is composed of barrel blocks which are individually thermostatable. The first two barrels can be thermostated for the purpose of better material intake. From the third barrel onward, it is preferable to establish a constant temperature which should be chosen so as to be material-specific and is dependent in particular on the melting point of the active substance used and on the glass transition temperature of the polymer. The resulting product temperature is, however, usually dependent on the degree of shearing of the screw element used and may in some cases be 20-30° C. higher than the barrel temperature set.

A devolatilization zone which is advantageously operated at ambient pressure can be present downstream of the melting zone.

The round dies used may have a diameter of from 0.5 to 5 mm. Other die shapes, such as slot dies, can likewise be used, especially when a greater material throughput is desired.

The two corotating screws are designed so that, downstream of a feed zone consisting of conveying elements, kneading blocks having a downstream flow restrictor are already used in the third heating zone. After a short decompression zone comprising conveying elements, the now molten material is thoroughly mixed again in a kneading zone. This is followed by a conveying element zone with downstream kneading elements. A conveying element zone with downstream kneading zone follows. Finally, the discharge of the material is ensured by a conveying element zone.

The resulting extrudates can be processed by means of a granulator to give pellets, and these in turn can be further comminuted (milled) to give a powder. The pellets or powder can be introduced into capsules or pressed to give tablets with the use of customary tableting assistants. In this case, it is also possible to use further excipients which control the release.

It is furthermore possible to use water, organic solvents, buffer substances or plasticizers during the extrusion. In particular, water or volatile alcohols are suitable for this purpose. This process permits reactions at relatively low temperature. The amounts of solvent or plasticizer are usually from 0 to 30% of the extrudable materials. The water or solvent can be removed through a devolatilization point in the extruder at atmospheric pressure or by application of reduced pressure. Alternatively, these components evaporate when the extrudate leaves the extruder and the pressure decreases to atmospheric pressure. In the case of sparingly volatile components, the extrudate can be subsequently dried in an appropriate manner.

In a particular variant of the preparation process, the thermoplastic material can be calendered, directly after the extrusion, to give a tablet-like compact which constitutes the final administration form. In this variant, it may be expedient to add further constituents, such as, for example, polymers for adjusting the glass transition temperature and the melt viscosity, disintegrants, solubilizers, plasticizers, dyes, flavorings, sweeteners, etc., before or during the extrusion. In principle, these substances may also be used when the extrudate is first comminuted and then pressed to give tablets.

Water-soluble polymers having a high glass transition temperature, such as, for example, polyvinylpyrrolidone having K values of 17-120, hydroxyalkylcelluloses or hydroxyalkyl-starches, can be used for adjusting the glass transition temperature of the formulation. An excessively high glass transition temperature of the formulation can be reduced by addition of plasticizers. All plasticizers which are also used for pharmaceutical coatings, such as, for example, triethyl citrate, tributyl citrate, acetyl tributyl citrate, triacetin, propylene glycol, polyethylene glycol 400, dibutyl sebacate, glyceryl monostearate, lauric acid, cetyl stearyl alcohol, are in principle suitable for this purpose.

Furthermore, surfactants which reduce the melt viscosity and hence the extrusion temperature can additionally be incorporated into the preparations. These substances can also positively influence the possible crystallization and bring about better wetting of the formulation and faster dissolution. Suitable substances are ionic and nonionic surfactants, such as, for example, Solutol® HS 15 (Macrogol 15 Hydroxystearate), Tween® 80, polyoxyethylated fatty acid derivatives, such as Cremophor® RH40 (Polyoxyl 40 Hydrogenated Castor Oil, USP), Cremophor EL (Polyoxyl 35 Castor Oil, USP), poloxamers, docusate sodium or sodium laurylsulfate.

The still plastic mixture is preferably extruded through a die, cooled and comminuted. In principle, all customary techniques known for this purpose, such as hot face cutting or cold face cutting, are suitable for the comminution.

The extrudate is face-cut, for example, by means of rotating blades or by means of an air jet and then cooled with air or under inert gas.

It is also possible to place the extrudate as a melt strand on a cooled belt (stainless steel, Teflon, chain belt) and to granulate it after solidification.

The extrudate can then optionally be milled. The preparations are obtained as free-flowing and flowable water-soluble powders. Particle sizes of from 20 to 250 μm are preferably established.

Furthermore, it is also possible to process the plastic mixture comprising the polymer and active substance by injection molding.

Surprisingly, the formulations according to the invention have considerably improved stability, i.e. the active substance remains in the molecularly disperse or colloidally disperse amorphous state in the formulation and does not crystallize. As a result, the release properties too do not change over time. If the particle size of the extrudates is above 300 μm, the effect of the slightly water-soluble polymer on the release is evident. In these cases, this means that the release is sustained or gastric resistant, depending on the addition. However, if the extrudate is comminuted so that the particle sizes are below 100 μm, a fast release is surprisingly achieved in the use of gastric resistant or sustained-release polymers.

The preparations according to the invention have a higher bioavailability of the active substance.

The preparations obtained by the process according to the invention can be used in principle in all areas where only slightly water-soluble or insoluble substances are to be used in aqueous preparations or to display their effect in an aqueous medium.

In the context of the present invention, slightly water-soluble substances are preferably to be understood as meaning biologically active substances, such as pharmaceutical active substances for humans and animals, cosmetic or agrochemical active substances or food supplements or dietary active substances.

Furthermore, dyes, such as inorganic or organic pigments, are also suitable as slightly soluble substances to be solubilized.

The extrusion temperatures are usually in the range from 50 to 260° C., preferably in the range of 70-200° C. The lower temperature limit depends on the composition of the mixtures to be extruded and on the slightly soluble substances to be processed in each case. At least part of the mixture must be plasticizable at the chosen temperature. The upper temperature limit is defined by the decomposition of the active substance or of the polymers.

The pharmaceutical active substances used are substances which are insoluble or sparingly soluble in water, according to the definition in DAB 9.

According to DAB 9 (German Pharmacopeia), the solubility of substances is classified as follows: sparingly soluble (soluble in from 30 to 100 parts of solvent); slightly soluble (soluble in from 100 to 1000 parts of solvent); practically insoluble (soluble in more than 10 000 parts of solvent), based in each case on one part of substance to be dissolved at 20° C.

The active substances may originate from any indication area.

Benzodiazepines, antihypertensives, vitamins, cytostatics—in particular taxol, anesthetics, neuroleptics, antidepressants, antiviral agents, such as, for example, anti-HIV agents, antibiotics, antimycotics, antidementives, fungicides, chemotherapeutics, urologicals, platelet aggregation inhibitors, sulfonamides, spasmolytics, hormones, immunoglobulins, sera, thyroid therapeutics, psychopharmaceuticals, antiparkinson agents and other antihyperkinetics, ophthalmologicals, neuropathy preparations, calcium metabolism regulators, muscle relaxants, lipid-lowering agents, liver therapeutics, coronary agents, cardiac agents, immunotherapeutics, regulatory peptides and their inhibitors, hypnotics, sedatives, gynecologicals, antigout agents, fibrinolytics, enzyme preparations and transport proteins, enzyme inhibitors, emetics, perfusion promoters, diuretics, diagnostics, corticoids, cholinergics, biliary therapeutics, antiasthmatics, bronchospasmolytics, beta-receptor blockers, calcium antagonists, ACE inhibitors, arteriosclerosis agents, anti-inflammatory agents, anticoagulants, antihypotensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists, weight-reducing agents may be mentioned here as examples.

Among the abovementioned pharmaceutical preparations, those which are orally administerable formulations are particularly preferred.

The content of the mixture of polyether copolymer and slightly soluble polymer in the pharmaceutical preparation is, depending on the active substance, in the range from 1 to 99% by weight, preferably from 5 to 80% by weight, particularly preferably from 10 to 70% by weight.

For the preparation of the pharmaceutical administration forms, such as, for example, tablets, customary pharmaceutical excipients may be added to the extrudates.

These are substances from the class consisting of fillers, plasticizers, solubilizers, binders, silicates and disintegrants and adsorbents, lubricants, flow improvers, dyes, stabilizers, such as antioxidants, wetting agents, preservatives, mold release agents, aromas or sweeteners, preferably fillers, plasticizers and solubilizers.

Fillers which may be added are, for example, inorganic fillers, such as oxides of magnesium, aluminum, silicon, titanium carbonate or calcium carbonate, calcium phosphates or magnesium phosphates, or organic fillers, such as lactose, sucrose, sorbitol, mannitol.

Suitable plasticizers are, for example, triacetin, triethyl citrate, glyceryl monostearate, low molecular weight polyethylene glycols or poloxamers.

Surface-active substances having an HLB value (hydrophilic-lipophilic balance) greater than 11, for example hydrogenated castor oil ethoxylated with 40 ethylene oxide units (Cremophor® RH 40), castor oil ethoxylated with 35 ethylene oxide units (Cremophor EL), polysorbate 80, poloxamers, docusate sodium or sodium laurylsulfate, are suitable as additional solubilizers.

Stearates of aluminum, calcium, magnesium and tin, and magnesium silicate, silicones and the like can be used as lubricants.

For example, talc or colloidal silica can be used as flow improvers.

For example, microcrystalline cellulose is suitable as a binder.

For additional adjustment of delayed release, further slightly water-soluble polymers may also be added to the tableting mixtures.

Disintegrants may be crosslinked polyvinylpyrrolidone or crosslinked sodium carboxymethyl-starch. Stabilizers may be ascorbic acid or tocopherol.

Dyes are, for example, iron oxides, titanium dioxide, triphenylmethane dyes, azo dyes, quinoline dyes, indigotin dyes, carotinoids, for coloring the administration forms, opacifying agents, such as titanium dioxide or talc, for increasing the light transmittance and decreasing the use of dyes.

In addition to use in cosmetics and pharmacy, the preparations produced according to the invention are also suitable for use in the food sector, for example for the incorporation of slightly water-soluble or water-insoluble nutrients, assistants or additives, such as, for example, fat-soluble vitamins or carotinoids. Beverages colored with carotinoids may be mentioned as examples.

The use of the preparations obtained according to the invention in agrochemistry may comprise, inter alia, formulations which comprise pesticides, herbicides, fungicides or insecticides, especially those preparations of crop protection agents to be used as formulations for spraying or watering.

So-called solid solutions of slightly soluble substances can be obtained with the aid of the process according to the invention. According to the invention, systems in which no crystalline fractions of the slightly soluble substance are observable are designated as solid solutions.

On visual assessment of the stable solid solutions, no amorphous constituents are evident. The visual assessment can be effected using an optical microscope, either with or without polarization filters under 40 times magnification.

Furthermore, the preparations can also be investigated with regard to crystallinity or amorphous properties with the aid of XRD (X-ray diffraction) and DSC (differential scanning calorimetry).

The preparations obtained by the process according to the invention are present, as stated, in amorphous form, which means that the crystalline fractions of the biologically active substance are less than 5% by weight. Preferably, the amorphous state is checked by means of DSC or XRD. Such an amorphous state may also be designated as X-ray amorphous state.

The process according to the invention permits the production of stable preparations having a high active substance loading and good stability with regard to the amorphous state of the slightly soluble substance.

The process according to the invention permits the production of stable preparations having a high active substance loading.

EXAMPLES

Preparation of Polymer 1

In a stirred apparatus, the initially taken mixture was heated to 77° C. under an $N_2$ atmosphere without the portion of feed 2. When the internal temperature of 77° C. was reached, the portion of feed 2 was added and prepolymerization was effected for 15 min. Thereafter, feed 1 was metered in 5 h and feed 2 in 2 h. After all feeds had been metered in, the reaction mixture was subsequently polymerized for a further 3 h. After subsequent polymerization, the solution was adjusted to a solids content of 50% by weight.

Initially taken mixture: 25 g of ethyl acetate
104.0 g of PEG 6000,
1.0 g of feed 2
Feed 1: 240 g of vinyl acetate
Feed 2: 456 g of vinylcaprolactam
240 g of ethyl acetate
Feed 3: 10.44 g of tert-butyl perpivalate (75% strength by weight in aliphatics mixture)
67.90 g of ethyl acetate.

Thereafter, the solvent was removed by a spray process and a pulverulent product was obtained. The K value was 16, measured as a 1% strength by weight solution in ethanol.

The twin-screw extruder which was used for the preparation of the formulations described in the following examples had a screw diameter of 16 mm and a length of 40D. The entire extruder was composed of 8 individual thermostatable barrel blocks. The first two barrels were thermostated at 20° C. and at 70° C., respectively, for the purpose of better material intake. From the third barrel onward, a constant temperature was established.

The solid solutions prepared were investigated by means of XRD (X-ray diffractometry) and DSC (differential scanning calorimetry) with regard to crystallinity and amorphous properties, using the following apparatuses and conditions:

XRD
Measuring apparatus: D 8 Advance diffractometer with 9-tube sample changer (from Bruker/AXS)
Measurement method: θ-θ geometry in reflection
2 theta angle range: 2-80°
Step width: 0.02°
Measuring time per angle step: 4.8 s
Divergence slit: Göbel mirror with 0.4 mm inserted aperture
Antiscattering slit: Soller slit
Detector: Sol-X detector
Temperature: room temperature
Generator setting: 40 kV/50 mA
DSC
DSC Q 2000 from TA-Instruments
Parameters:
Weight taken about 8.5 mg
Heating rate: 20K/min The active substance release was effected according to the USP apparatus (paddle method 2), 37° C., 50 rpm (BTWS 600, Pharmatest). The extrudates were comminuted to a length of 3 mm by means of a granulator and were introduced into hard gelatin capsules. The detection of the active substance released was effected by UV spectroscopy (Lamda-2, Perkin Elmer).

Example 1

1200 g of polymer 1, 400 g of Eudragit E PO and 400 g of Celecoxib (melting point 162° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel onward: 140° C.
Screw speed 200 rpm
Throughput: 500 g/h
Die diameter 3 mm The solid solutions were investigated by XRD and by DSC and were found to be amorphous. After 1 h in 0.1 normal HCl, 95% of active substance had been released. After storage for 6 months at 30° C./70% relative humidity, the preparations were still amorphous.

Example 2

800 g of polymer 1, 800 g of Eudragit E PO and 400 g of Naproxen (melting point 157° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel onward: 120° C.
Screw speed 200 rpm
Throughput: 600 g/h
Die diameter 3 mm The solid solutions were investigated by XRD and by DSC and found to be amorphous. After 1 h in 0.1 normal HCl, 89% of active substance had been released.

Example 3

1200 g of polymer 1, 400 g of Eudragit E PO, 40 g of sodium laurylsulfate and 400 g of itraconazole (melting point 166° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 140° C.
Screw speed 200 rpm
Throughput: 800 g/h
Dye diameter 3 mm The solid solutions were investigated by XRD and by DSC and found to be amorphous. After 1 h in 0.1 normal HCl, 99% of active substance had been released.

After storage for 6 months at 30° C./70% relative humidity, the preparations were still amorphous.

Example 4

600 g of polymer 1, 1000 g of Kollidon SR and 400 g of fenofibrate (melting point 81° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 110° C.
Screw speed 200 rpm
Throughput: 1000 g/h
Dye diameter 3 mm The solid solutions were investigated by XRD and by DSC and found to be amorphous. The release of the active substance in 0.1 normal HCl after 2 h was less than 20%. After rebuffering to pH 6.8, this was for a further 10 h, after which altogether 80% of active substance was released.

After storage for 6 months at 30° C./70% relative humidity, the preparations were still amorphous.

Example 5

600 g of polymer 1, 1000 g of Eudragit S 100 and 400 g of cinnarizine (melting point 122° C.) were weighed into a Turbula mixing container and mixed for 10 minutes in the Turbula mixer T10B. Triethyl citrate was fed into the extruder via a reciprocating piston pump.

The mixture was extruded under the following conditions:
Zone temperature of 1st barrel: 20° C.; 2nd barrel: 40° C.
Zone temperature from the 3rd barrel: 130° C.
Screw speed 100 rpm
Throughput: 800 g/h
Liquid metering: 80 g/h
Dye diameter 3 mm The solid solutions were investigated by XRD and by DSC and found to be amorphous. The release of the active substance in 0.1 normal HCl after 2 h was less than 10%; after rebuffering to pH 6.8, 100% were released.

After storage for 6 months at 30° C./70% relative humidity, the preparations were still amorphous.

Example 6

400 g of polymer 1, 1200 g of Eudragit E PO and 400 g of carbamazepine (melting point 192° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 160° C.
Screw speed 200 rpm
Throughput: 600 g/h
Dye diameter 3 mm The solid solutions were investigated by XRD and by DSC and found to be amorphous. After 1 h in 0.1 normal HCl, 95% of active substance had been released.

After storage for 6 months at 30° C./70% relative humidity, the preparations were still amorphous.

Example 7

600 g of polymer 1, 1000 g of Eudragit L 100-55 and 400 g of loperamide (melting point 223° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 170° C.
Screw speed 200 rpm
Throughput: 1000 g/h
Dye diameter 3 mm The solid solutions were investigated by XRD and by DSC and found to be amorphous. The release of the active substance in 0.1 normal HCl after 2 h was less than 10%; after rebuffering to pH 6.8, 98% were released.

After storage for 6 months at 30° C./70% relative humidity, the preparations were still amorphous.

Example 8

600 g of polymer 1, 500 g of Eudragit RS PO, 500 g of Eudragit RL PO and 400 g of clotrimazole (melting point 148° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 150° C.
Screw speed 100 rpm
Throughput: 700 g/h
Dye diameter 3 mm The solid solutions were investigated by XRD and by DSC and found to be amorphous. The release of the active substance in phosphate buffer pH 6.8 was 20% after 2 h; after 10 h, 84% of the active substance originally used had been released.

After storage for 6 months at 30° C., the preparations were still amorphous.

Example 9

600 g of polymer 1, 1000 g of HPMCAS (hydroxypropyl methylcellulose acetate succinate) and 400 g of cinnarizine (melting point 122° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 140° C.
Screw speed 100 rpm
Throughput: 800 g/h
Dye diameter 3 mm The solid solutions were investigated by XRD and by DSC and found to be amorphous. The release of the active substance in 0.1 normal HCl after 2 h was less than 10%; after rebuffering to pH 6.8, 90% were released.

After storage for 6 months at 30° C./70% relative humidity, the preparations were still amorphous.

Example 10

600 g of polymer 1, 500 g of Eudragit RS PO, 500 g of Eudragit RL PO and 400 g of piroxicam (melting point 199° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 170° C.
Screw speed 100 rpm
Throughput: 700 g/h
Dye diameter 3 mm The solid solutions were investigated by XRD and by DSC and found to be amorphous. The release of the active substance in phosphate buffer pH 6.8 was 20% after 2 h; after 10 h, 93% of the active substance originally used had been released.

After storage for 6 months at 30° C./70% relative humidity, the preparations were still amorphous.

Example 11

600 g of polymer 1, 1000 g of ethylcellulose and 400 g of felodipine (melting point 145° C.) were weighed into a Turbula mixing container and mixed for 10 minutes in the Turbula mixer T10B. Eudragit NE 40D was fed into the extruder via a reciprocating piston pump.

The mixture was extruded under the following conditions:
Zone temperature of 1st barrel: 20° C.; 2nd barrel: 40° C.
Zone temperature from the 3rd barrel: 140° C.
Screw speed 100 rpm
Throughput: 800 g/h
Liquid metering: 60 g/h
Dye diameter 3 mm The solid solutions were investigated by XRD and by DSC and found to be amorphous. The release of the active substance in phosphate buffer pH 6.8 was 31% after 2 h; after 10 h, 79% of the active substance originally used had been released.

After storage for 6 months at 30° C./70% relative humidity, the preparations were still amorphous.

Example 12

600 g of polymer 1, 1000 g of Eudragit RS PO and 400 g of itraconazole (melting point 166° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 150° C.
Screw speed 100 rpm
Throughput: 800 g/h
Dye diameter 3 mm The solid solutions were investigated by XRD and by DSC and found to be amorphous. The release of the active substance in phosphate buffer pH 6.8 was 27% after 2 h; after 10 h, 82% of the active substance originally used had been released.

After storage for 6 months at 30° C./70% relative humidity, the preparations were still amorphous.

Example 13

400 g of polymer 1, 1200 g of Eudragit RL PO and 400 g of carbamazepine (melting point 192° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 160° C.
Screw speed 100 rpm
Throughput: 800 g/h
Dye diameter 3 mm The solid solutions were investigated by XRD and by DSC and found to be amorphous. The release of the active substance in HCl after 2 h was less than 20%. After rebuffering to pH 6.8, 75% were released after 10 h.

After storage for 6 months at 30° C./70% relative humidity, the preparations were still amorphous.

Example 14

1200 g of polymer 1, 400 g of Eudragit E PO, 20 g of docusate sodium and 400 g of fenofibrate (melting point 81° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 120° C.
Screw speed 100 rpm
Throughput: 800 g/h
Dye diameter 3 mm The solid solutions were investigated by XRD and by DSC and found to be amorphous. The release of the active substance in HCl after 2 h was 83%.

After storage for 6 months at 30° C., the preparations were still amorphous.

Example 15

600 g of polymer 1, 500 g of Kollidon SR, 500 g of ethylcellulose, 20 g of Cremophor RH40 and 400 g of clotrimazole (melting point 148° C.) were weighed into a Turbula mixing container and mixed for 10 minutes in the Turbula mixer T10B.

Kollidon SR: physical mixture of 80% by weight of polyvinyl acetate, 19% by weight of polyvinylpyrrolidone k30, 0.8% by weight of sodium laurylsulfate, 0.2% by weight of silicon dioxide.

The mixture was extruded under the following conditions:
Zone temperature of 1st barrel: 20° C.; 2nd barrel: 40° C.
Zone temperature from the 3rd barrel: 160° C.
Screw speed 100 rpm
Throughput: 700 g/h
Dye diameter 3 mm The solid solutions were investigated by XRD and by DSC and found to be amorphous. The release of the active substance in 0.1 normal HCl after 2 h was less than 20%.

After rebuffering to pH 6.8, 87% were released after 10 h.

After storage for 6 months at 30° C./70% relative humidity, the preparations were still amorphous.

Example 16

600 g of polymer 1, 1000 g of HPMCAS and 400 g of fenofibrate (melting point 81° C.) were weighed into a Turbula mixing container and mixed for 10 minutes in the Turbula mixer T10B.

The mixture was extruded under the following conditions:
Zone temperature of 1st barrel: 20° C.; 2nd barrel: 40° C.
Zone temperature from the 3rd barrel: 120° C.
Screw speed 100 rpm
Throughput: 800 g/h
Dye diameter 3 mm The solid solutions were investigated by XRD and by DSC and found to be amorphous. The release of the active substance in 0.1 normal HCl after 2 h was less than 10%; after rebuffering to pH 6.8, 100% were released.

Example 17

The extrudate from Example 7 was comminuted by means of an air jet mill to a particle size of less than 25 μm. The release of the active substance in 0.1 normal HCl after 1 h was 82%.

Example 18

The extrudate from Example 15 was comminuted by means of an air jet mill to a particle size of less than 20 μm. The release of the active substance in 0.1 normal HCl after 1 h was 79%.

We claim:
1. A dosage form comprising preparations of slightly water-soluble active substances in a polymer matrix comprising a polyether copolymer and at least one slightly water-soluble polymer, the polyether copolymer being obtained by free radical polymerization of a mixture of from 30 to 80% by weight of N-vinyllactam, from 10 to 50% by weight of vinyl acetate and from 10 to 50% by weight of a polyether, wherein the slightly water-soluble polymers are based on ethyl acrylate and methyl methacrylate, wherein the slightly water-soluble active substance is present in amorphous form in the polymer matrix, and wherein the preparations remain amorphous after storage for 6 months at 30° C./70% relative humidity.

2. The dosage form according to claim 1, wherein the slightly water-soluble polymers comprise those polymers whose solubility in water is pH-dependent.

3. The dosage form according to claim 1, wherein the ratio of the polyether copolymer to the slightly water-soluble polymer is from 99:1 to 10:90.

4. The dosage form according to claim 1, wherein the ratio of the polyether copolymer to the slightly water-soluble polymer is from 90:10 to 30:70.

5. The dosage form according to claim 1, wherein the ratio of the polyether copolymer to the slightly water-soluble polymer is from 80:20 to 40:60.

6. The dosage form according to claim 1, in which the polymer matrix further comprises a solubilizer.

7. A process for the production of preparations for dosage forms of slightly water-soluble active substances according to claim 1, wherein the active substances are present in amorphous form embedded in a polymer matrix based on polyether copolymers of from 30 to 80% by weight of N-vinyllactam, from 10 to 50% by weight of vinyl acetate and from 10 to 50% by weight of a polyether, wherein, in addition to the polyether copolymer, at least one slightly water-soluble polymer based on ethyl acrylate and methyl methacrylate, is incorporated into the polymer matrix, and the polymers are thoroughly mixed with the slightly water-soluble active substances, and wherein the preparations remain amorphous after storage for 6 months at 30° C./70% relative humidity.

8. The process according to claim 7, wherein the mixture of polymers and active substances is heated above the glass transition temperature of the polyether copolymers.

9. The process according to claim 7, wherein the mixing of polymers and active substances is effected in an extruder.

10. The process according to claim 7, wherein the mixing of polymers and active substances is effected in organic solution, and the organic solvents are then removed.

11. The process according to claim 10, wherein the organic solvents are removed by spray drying.

* * * * *